United States Patent
Mitsuhashi et al.

(10) Patent No.: US 9,687,422 B2
(45) Date of Patent: Jun. 27, 2017

(54) METHOD FOR PRODUCING CAROTENOID-CONTAINING COMPOSITION, AND CAROTENOID-CONTAINING COMPOSITION

(71) Applicants: DAICEL CORPORATION, Osaka-shi, Osaka (JP); JX NIPPON OIL & ENERGY CORPORATION, Tokyo (JP)

(72) Inventors: Kazuya Mitsuhashi, Myoko (JP); Takanori Someya, Myoko (JP); Motoko Hayashi, Myoko (JP); Manabu Yamada, Myoko (JP); Shotaro Uchizawa, Tokyo (JP); Kazuaki Hirasawa, Tokyo (JP); Yuki Kawashima, Tokyo (JP)

(73) Assignees: JX NIPPON OIL & ENERGY CORPORATION, Tokyo (JP); DAICEL CORPORATION, Osaka-Shi, Osaka (JP)

( * ) Notice: Subject to any disclaimer, the term of this patent is extended or adjusted under 35 U.S.C. 154(b) by 0 days.

(21) Appl. No.: 14/432,946

(22) PCT Filed: Oct. 2, 2013

(86) PCT No.: PCT/JP2013/076774
§ 371 (c)(1),
(2) Date: Apr. 1, 2015

(87) PCT Pub. No.: WO2014/054669
PCT Pub. Date: Apr. 10, 2014

(65) Prior Publication Data
US 2015/0272835 A1    Oct. 1, 2015

(30) Foreign Application Priority Data

Oct. 2, 2012   (JP) ................................ 2012-220046

(51) Int. Cl.
*A61Q 19/00*   (2006.01)
*C07C 403/24*   (2006.01)
(Continued)

(52) U.S. Cl.
CPC .............. *A61K 8/0204* (2013.01); *A23L 5/44* (2016.08); *A61K 8/027* (2013.01); *A61K 8/31* (2013.01);
(Continued)

(58) Field of Classification Search
CPC . A23L 1/2753; A23V 2002/00; A61K 8/0204; A61Q 19/00; C07C 2101/16; C07C 403/24; C12P 23/00
See application file for complete search history.

(56) References Cited

U.S. PATENT DOCUMENTS

| 5,591,343 | A | 1/1997 | Kitaoka et al. |
| 7,563,935 | B2* | 7/2009 | Leigh .................... C07C 403/24 568/345 |
| 2011/0180010 | A1* | 7/2011 | Guo ..................... A23K 1/1606 119/230 |

FOREIGN PATENT DOCUMENTS

| EP | 0670306 A1 | 9/1995 |
| EP | 0732378 A2 | 9/1996 |

(Continued)

OTHER PUBLICATIONS

Crystal definition [online] retrieved on Mar. 14, 2016 from: http://www.oxforddictionaries.com/us/definition/american_english/crystal; 1 page.*

(Continued)

*Primary Examiner* — Ernst V Arnold
(74) *Attorney, Agent, or Firm* — Saliwanchik, Lloyd & Eisenschenk

(57) ABSTRACT

Methods of obtaining a carotenoid-containing composition were developed, in which degradation of carotenoids is (Continued)

suppressed even though extraction and purification are performed on a culture of microorganism that produces carotenoids including astaxanthin by simple steps using a lower alcohol which is a conventionally known solvent, and the compositions have high astaxanthin content and contain highly pure carotenoids and also have satisfactory crystal properties. Further addition of a simple step that promotes isomerization of astaxanthin successfully improved the carotenoid yield.

9 Claims, 3 Drawing Sheets

(51) Int. Cl.
  *C12P 23/00* (2006.01)
  *A61K 8/02* (2006.01)
  *A23L 5/44* (2016.01)
  *A61K 8/31* (2006.01)
  *A61K 8/99* (2017.01)
(52) U.S. Cl.
  CPC ............... *A61K 8/99* (2013.01); *A61Q 19/00* (2013.01); *C07C 403/24* (2013.01); *C12P 23/00* (2013.01); *A23V 2002/00* (2013.01); *A61K 2800/10* (2013.01); *C07C 2101/16* (2013.01)

(56) References Cited

FOREIGN PATENT DOCUMENTS

| | | |
|---|---|---|
| EP | 2 017 262 A1 | 1/2009 |
| EP | 2 090 182 A1 | 8/2009 |
| EP | 2 192 191 A1 | 6/2010 |
| EP | 2 402 455 A1 | 1/2012 |
| JP | H07-242621 A | 9/1995 |
| JP | H08-009964 A | 1/1996 |
| JP | H08-089280 A | 4/1996 |
| JP | H08-253695 A | 10/1996 |
| JP | 2004-208504 | 7/2004 |
| JP | 2007-319015 A | 12/2007 |
| JP | 2009-050237 A | 3/2009 |
| JP | 2009-201503 A | 9/2009 |

OTHER PUBLICATIONS

Saito (Statistical Physics of Crystal Growth 1996, World Scientific. 21 parabolic Crystal; 1 page).*
Zagalsky, P.F. "Crystallisation of Astaxanthin—Proteins of *Velella velella* (Coelenterata: Chondrophora)," *Comparative Biochemistry and Physiology*, 1982, 71B(2): 235-236.
International Search Report issued in corresponding PCT Application No. PCT/JP2013/076774, dated Jan. 7, 2014.

* cited by examiner

```
SEQUENCE LISTING

<160> NUMBER OF SEQ ID NOS: 1

<210> SEQ ID NO 1
<211> LENGTH: 1452
<212> TYPE: DNA
<213> ORGANISM: Unknown
<220> FEATURE:
<223> OTHER INFORMATION: E-396 bacterial strain
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
aatagccccg ggaaactggg agtaataccg tatacgccct ttgggggaaa gatttatcgg     180
agaaggatcg gcccgcgttg gattaggtag ttggtggggt aatggcccac caagccgacg     240
atccatagct ggtttgagag gatgatcagc cacactggga ctgagacacg gcccagactc     300
ctacgggagg cagcagtggg gaatcttaga caatggggggc aaccctgatc tagccatgcc     360
gcgtgagtga tgaaggcctt agggttgtaa agctctttca gctgggaaga taatgacggt     420
accagcagaa gaagccccgg ctaactccgt gccagcagcc gcggtaatac ggaggggggct     480 agcgttgttc ggaattactg ggcgtaaagc gcacgtaggc ggactggaaa gtcagaggtg     540
aaatcccagg gctcaacctt ggaactgcct ttgaaactat cagtctggag ttcgagagag     600
gtgagtggaa ttccgagtgt agaggtgaaa ttcgtagata tcggaggaa ccagtggc      660 gaaggcggct cactggctcg atactgacgc tgaggtgcga aagcgtgggg agcaaacagg     720
attagatacc ctggtagtcc acgccgtaaa cgatgaatgc cagacgtcgg caagcatgct     780
tgtcggtgtc acacctaacg gattaagcat tccgcctggg gagtacggtc gcaagattaa     840
aactcaaagg aattgacggg ggcccgcaca agcggtggag catgtggttt aattcgaagc     900
aacgcgcaga accttaccaa cccttgacat ggcaggaccg ctggagagat tcagctttct     960
cgtaagagac ctgcacacag gtgctgcatg gctgtcgtca gctcgtgtcg tgagatgttc    1020
ggttaagtcc ggcaacgagc gcaacccacg tccctagttg ccagcaattc agttgggaac    1080
tctatggaaa ctgccgatga taagtcggag gaaggtgtgg atgacgtcaa gtcctcatgg    1140
gccttacggg ttgggctaca cacgtgctac aatggtggtg acagtgggtt aatccccaaa    1200
```

-continued

```
agccatctca gttcggattg tcctctgcaa ctcgagggca tgaagttgga atcgctagta    1260
atcgcggaac agcatgccgc ggtgaatacg ttcccgggcc ttgtacacac cgcccgtcac    1320
accatgggag ttggttctac ccgacgacgn tgcgctaacc ttcgggggc aggcggccac     1380 ggtaggatca gcgactgggg tgaagtcgta acaaggtagc cgtaggggaa cctgcggctg    1440
gatcacctcc tt                                                        1452
```

METHOD FOR PRODUCING CAROTENOID-CONTAINING COMPOSITION, AND CAROTENOID-CONTAINING COMPOSITION

CROSS REFERENCE TO A RELATED APPLICATION

This application is a National Stage Application of International Application Number PCT/JP2013/076774, filed Oct. 2, 2013; which claims priority to Japanese Patent Application No. 2012-220046, filed Oct. 2, 2012, both of which are incorporated herein by reference in their entirety.

The Sequence Listing for this application is labeled "SEQ-LIST-3-25-15.txt", which was created on Mar. 25, 2015, and is 3 KB. The entire content is incorporated herein by reference in its entirety.

TECHNICAL FIELD

The present invention relates to methods of producing microorganism-derived compositions which contain carotenoids including astaxanthin. The present invention also relates to microorganism-derived compositions which contain carotenoids including astaxanthin, and which are needle crystals or needle-like crystals.

BACKGROUND ART

Carotenoids are natural pigments widely present in the natural world. They are polyene pigments having a color in the range of yellow to red or purple. Astaxanthin is one type of naturally-occurring carotenoid that exists in a free state or as an ester, or as various types of pigment proteins upon binding with proteins.

Astaxanthin is widely used as a coloring agent for fish and for chicken eggs. Astaxanthin is also approved as a food additive and is widely used in fat and oil-processed foods, protein foods, aqueous liquid foods, etc. Furthermore, astaxanthin has an antioxidant activity against peroxidation of lipids induced by free radicals, a singlet oxygen-scavenging action which is several hundred times stronger than that of α-tocopherol, or the like; therefore, astaxanthin is expected to be used in functional foods, cosmetic products, or pharmaceuticals by utilizing the strong antioxidant activity.

Astaxanthin is distributed widely in the natural world, for example, in fishes such as salmon, trout and red sea bream; and crustaceans such as crab, shrimp, and krill. Astaxanthin is also produced by microorganisms such as bacteria belonging to the genera *Agrobacterium, Brevibacterium, Paracoccus, Brevundimonas, Erythrobacter;* the genus *Haematococcus* green algae; and the genus *Phaffia* yeasts. Carotenoids such as astaxanthin, zeaxanthin or the like are industrially produced by a chemical synthesis method, but naturally-derived carotenoids are desired in terms of safety.

With such a background, many methods for producing carotenoids containing astaxanthin especially derived from microorganisms such as green algae or yeasts, which are considered to be suitable for mass production, have been reported. However, since green algae and yeasts have low carotenoid productivity and have a strong cell wall, carotenoid extraction from their cultures is difficult.

On the other hand, bacteria belonging to the genus *Paracoccus* have advantages such as having a high carotenoid productivity, having great proliferation speed, and easy carotenoid extraction.

The E-396 strain (FERM BP-4283: deposited on Apr. 27, 1993 (date of original deposition), International Patent Organism Depositary, National Institute of Advanced Industrial Science and Technology, (Chuoh 6, Higashi 1-1-1, Tsukuba City, Ibaraki Prefecture, Japan)) is known as an example of an astaxanthin-producing bacterial strain belonging to the genus *Paracoccus* (Patent Document 1). Reported methods for obtaining a purified carotenoid-containing composition from this bacterial strain include: a method which performs extraction by contacting the bacterial cells with a cyclic hydrophilic organic compound, which is not favorable for use in production of food or such in terms of safety (Patent Document 2); a method using supercritical fluid extraction (Patent Document 3); a method in which bacterial cells are contacted with a water-soluble organic solvent, a non-polar solvent, and water to perform liquid-liquid extraction (Patent Document 4); and also a method of extraction by contacting bacterial cells with lower alcohols, then washing precipitates obtained by concentrating the extract using water-containing lower alcohols (Patent Documents 5 and 6).

PRIOR ART DOCUMENTS

Patent Documents

[Patent Document 1] Japanese Patent Application Kokai Publication No. (JP-A) H08-9964 (unexamined, published Japanese patent application)
[Patent Document 2] JP-A (Kokai) H07-242621
[Patent Document 3] JP-A (Kokai) H08-89280
[Patent Document 4] JP-A (Kokai) H08-253695
[Patent Document 5] JP-A (Kokai) 2007-319015
[Patent Document 6] JP-A (Kokai) 2009-50237

SUMMARY OF THE INVENTION

Problems to be Solved by the Invention

Each of the above-mentioned conventional technologies are problematic in that: a solvent undesirable in terms of safety is used in the extraction/purification step; the extraction/purification step is complicated; a step of suspending and washing the obtained crystals in a solvent such as an alcohol-containing water is required; an organic solvent waste solution containing large amounts of water is generated and its treatment is necessary; it is difficult to obtain a carotenoid-containing composition having sufficiently high astaxanthin content and carotenoid purity at a high yield; and handling is complicated due to unfavorable crystal properties of the obtained carotenoid-containing composition; and such.

The present invention has been made in view of the problems of the above-mentioned conventional technology. An objective of the present invention is to provide methods of producing carotenoid-containing compositions that can give a high yield of a carotenoid-containing composition that is derived from a microorganism, have a high astaxanthin content and contain highly pure carotenoids, and also have satisfactory crystal properties, through simple steps using economical and safe solvents; and the aforementioned carotenoid-containing composition produced thereby.

Means for Solving the Problems

The present inventors developed methods of obtaining carotenoid-containing compositions from a culture of microorganism that produces carotenoids including astaxanthin, wherein degradation of carotenoids is suppressed, and wherein the carotenoid-containing compositions have a high astaxanthin content and contain highly pure carotenoids, as well as have satisfactory crystal properties, even though extraction and purification are performed by a simple step using a lower alcohol which is a conventionally-known solvent. Furthermore, the present inventors succeeded in improving carotenoid yield by adding a simple step that promotes isomerization of astaxanthin.

More specifically, the present invention comprises:

[1] a method of producing a carotenoid-containing composition which is a needle crystal or a needle-like crystal having a maximum length of 5 μm or longer, and whose astaxanthin content based on the total composition is 40 mass % or more, wherein the method comprises:
 an extraction step where a culture obtained by culturing a microorganism that produces carotenoids including astaxanthin is extracted using a one- to three-carbon alcohol;
 an extract separation step where an extract is obtained by separating the microorganism and the extract;
 a concentration step where a concentrate is obtained by concentrating the extract by 1.25-times to 20-times in terms of liquid quantity;
 a crystallization step where crystals of the carotenoid-containing composition is produced in the concentrate; and
 a crystal separation step where the crystals are separated and obtained from mother liquor;

[2] the method of producing a carotenoid-containing composition of [1], wherein the concentration ratio is less than ten-times in the concentration step;

[3] the production method of [1] or [2], which further comprises a heating step where prior to subjecting the concentrate to the crystallization step, the solution is heated to a temperature higher than the temperature for the crystallization step;

[4] the production method of [3], which further comprises a step selected from the group consisting of: a water-addition step where water is added to the concentrate before the heating step; a water-addition step where water is added to the concentrate during the concentration step; and a water-addition step where water is added to the extract separated from the microorganism before the concentration step;

[5] the production method of [3] or [4], wherein the temperature used in the heating step is 40° C. to 70° C.;

[6] a carotenoid-containing composition derived from a microorganism that produces carotenoids including astaxanthin, wherein the astaxanthin content based on the mass of the total composition is 40 mass % or more, and the carotenoid-containing composition is a needle crystal or a needle-like crystal having a maximum length of 5 μm or longer; and

[7] the carotenoid-containing composition of [6], which is produced by a production method of any one of [1] to [5].

MODE FOR CARRYING OUT THE INVENTION

Figure 1:
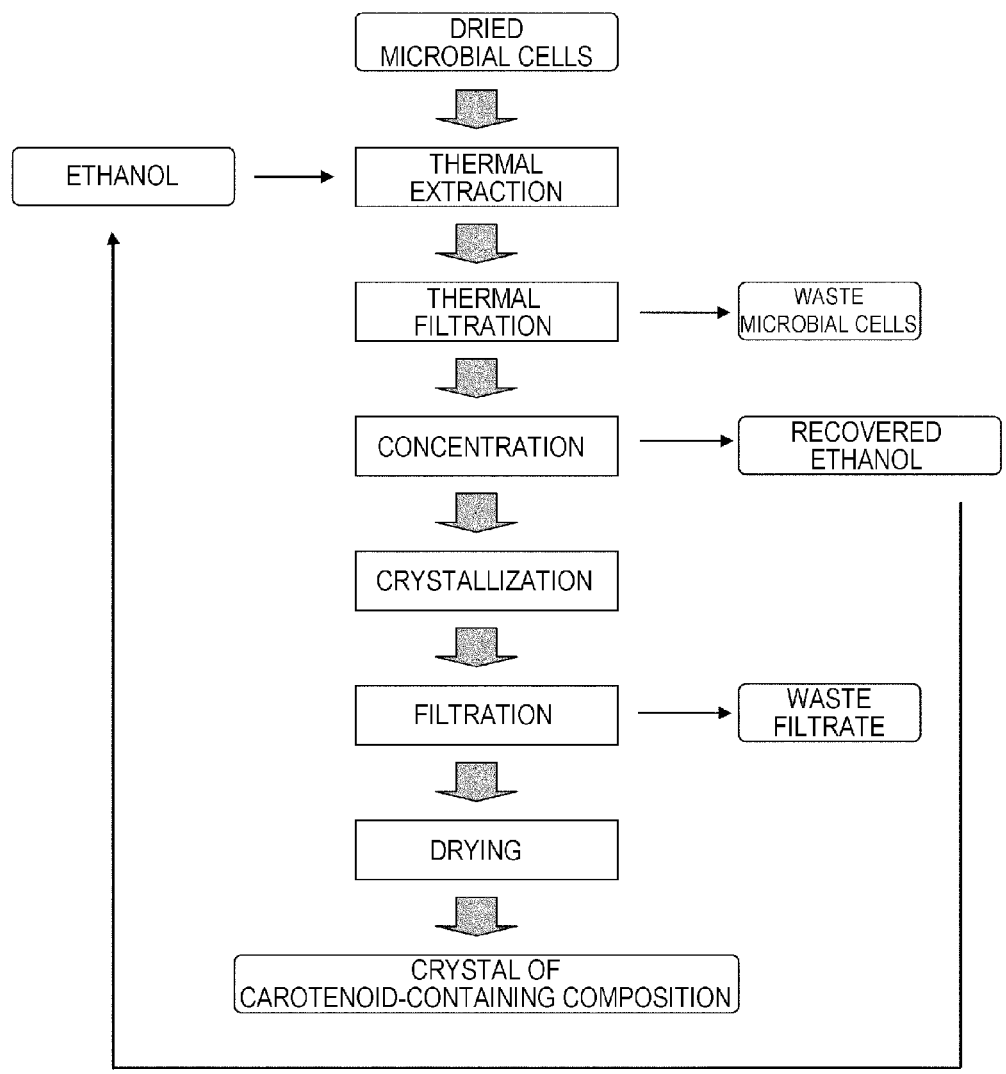
FIG. 1 shows an embodiment of the present invention for producing a composition which contains carotenoids including astaxanthin from dried microbial cells which contain carotenoids including astaxanthin.

Hereinafter, the present invention will be specifically illustrated by examples of preferred embodiments. The scope of the present invention is not restricted to the following description, and in addition to the following examples of embodiments, the present invention may be carried out by making appropriate modifications without departing from the essence of the present invention.

The method of this embodiment, which is a method of producing a carotenoid-containing composition which is a needle crystal or a needle-like crystal having a maximum length of 5 μm or longer, and whose astaxanthin content based on the total composition is 40 mass % or more, is a method comprising:
 an extraction step where a culture obtained by culturing a microorganism which produces carotenoid including astaxanthin is extracted using a one- to three-carbon alcohol;
 an extract separation step where an extract is obtained by separating the microorganism and the extract;
 a concentration step where a concentrate is obtained by concentrating the extract 1.25-times to 20-times in terms of liquid quantity;
 a crystallization step where crystals of carotenoid-containing composition is generated in the concentrate; and
 a crystal separation step where the crystals are separated from mother liquor.

The carotenoid-containing composition obtained by the production method of this embodiment has an astaxanthin content with respect to the mass of the entire composition of preferably 40 mass % or more, more preferably 50 mass % or more, and most preferably 55% or more.

The aforementioned composition is also a needle crystal or a needle-like crystal having a maximum length longer than 2 μm, preferably 5 μm or longer, more preferably 7 μm or longer, and most preferably 10 μm or longer. The crystal lengths do not have to be uniform and may comprise, for example, 3 μm to 10 μm long needle crystals or needle-like crystals. Here, maximum crystal length refers to the largest crystal length of a subject observed in a visual field through a means of magnification, such as a microscope.

[Production and Extraction of a Carotenoid-Containing Composition, and its Separation from Microbial Cells]

(Carotenoid-Producing Microorganisms and Culturing of such Microorganisms)

Carotenoid-producing microorganisms that constitute cultures according to the production method of this embodiment are not limited at all as long as they are microorganisms that produce a carotenoid including astaxanthin; however, microorganisms belonging to the genera *Agrobacterium*, *Brevibacterium*, *Paracoccus*, *Brevundimonas*, and *Erythrobacter*, and algae belonging to the genus *Haematococcus*, yeast belonging to the genus *Phaffia*, and such may be used.

Of these microorganisms, from the viewpoint of the proliferation speed and carotenoid productivity, a bacterium of which the DNA nucleotide sequence corresponding to 16S ribosomal RNA is substantially homologous to the nucleotide sequence represented by SEQ ID NO: 1 is preferable. The expression "substantially homologous" means that these sequences have a homology of 94% or higher, preferably 96% or higher, and more preferably 98% or higher, considering the error frequency in determining the nucleotide sequence of DNA, and the like. Among such bacteria, the E-396 strain (FERM BP-4283) is particularly preferable. A highly preferable example is a strain that gives a high carotenoid production, which is obtained by mutating these microorganisms and is selected for the purpose of improving carotenoid productivity.

The E-396 strain is deposited as an international deposition with the International Patent Organism Depositary, National Institute of Advanced Industrial Science and Technology as follows:

International Deposition Authority: International Patent Organism Depositary, National Institute of Advanced Industrial Science and Technology (former National Institute of Bioscience and Human-Technology, Agency of Industrial Science and Technology, Ministry of International Trade and Industry)

Chuoh 6, Higashi 1-1-1, Tsukuba City, Ibaraki Prefecture, 305-8566

Identification No.: E-396

Deposition No.: FERM BP-4283

Date of original deposition: Apr. 27, 1993

There is no specific limitation on the method for producing a mutant as long as the method induces mutation. Usable methods include, for example, a chemical method using a mutating agent such as N-methyl-N'-nitro-N-nitrosoguanidine (NTG), ethylmethanesulfonate (EMS); a physical method such as ultraviolet radiation, x-ray radiation; or a biological method by gene recombination, transposon or the like. This mutation treatment may be performed once or it may be performed two or more times, for example, by obtaining a mutant of a carotenoid-producing microorganism by the mutation treatment and then further subjecting this to mutation treatment(s).

The culture of a carotenoid-producing microorganism to be used in the culturing step of the production method of this embodiment is not limited at all as long as it is a culture that can be obtained by using a method that can efficiently culture the above-mentioned microorganisms, such as a method that uses the following media to perform the culturing by a liquid culture, solid culture, or a combination thereof.

As a nutrient medium to be used in culturing the carotenoid-producing microorganisms of the production method of this embodiment, a nutrient medium containing carbon sources, nitrogen sources, and inorganic salts necessary for growth of the microorganism is sufficient, but addition of vitamins may be more preferable in some cases. It may be preferable to further add amino acids, nucleobase or the like. Other substances which may be optionally added include yeast extract, peptone, meat extract, malt extract, corn steep liquor, dry yeast, soybean cake and the like.

Usable carbon sources include sugars such as glucose, sucrose, lactose, fructose, trehalose, mannose, mannitol, and maltose; organic acids such as acetic acid, fumaric acid, citric acid, propionic acid, malic acid, malonic acid, and pyruvic acid; alcohols such as ethanol, propanol, butanol, pentanol, hexanol, isobutanol, and glycerol; fats and oils such as soybean oil, rice bran oil, olive oil, corn oil, sesame oil, and linseed oil; etc. These carbon sources may be used independently or in a combination of two or more. The ratio thereof depends on the type of the carbon source and may be appropriately adjusted, but usually is 1 g to 100 g, preferably 2 g to 50 g, per 1 L of the medium.

Usable nitrogen sources include, for example, potassium nitrate, ammonium nitrate, ammonium sulfate, ammonium chloride, ammonium phosphate, ammonia, and urea. These nitrogen sources may be used independently or in a combination of two or more. The ratio thereof depends on the type of the nitrogen source and may be appropriately adjusted, but usually is 0.1 g to 30 g, preferably 1 g to 10 g, per 1 L of the medium.

Usable inorganic salts include potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium carbonate. These inorganic salts may be used independently or in a combination of two or more. The ratio thereof depends on the type of the inorganic salt and may be appropriately adjusted, but usually is 0.001 g to 10 g, per 1 L of the medium.

When vitamins are added, the amount thereof depends on the type of the vitamins and may be appropriately adjusted, but usually is 0.1 mg to 1000 mg, preferably 1 mg to 100 mg, per 1 L of the medium.

The amount of each of amino acid, nucleobase, yeast extract, peptone, meat extract, malt extract, corn steep liquor, dry yeast, soybean cake and the like depends on the type of the substance and may be appropriately adjusted, but usually is 0.2 g to 200 g, preferably 3 g to 100 g, per 1 L of the medium.

The pH of the medium is adjusted to 2 to 12, preferably 6 to 9. The culturing is performed at a temperature of 15° C. to 80° C., preferably 20° C. to 35° C., generally for 1 day to 20 days, preferably for 2 days to 8 days, under an aerobic condition. The aerobic condition includes, for example, shaking culture, aeration and stirring culture.

In the production method of this embodiment, when extracting carotenoids produced by the carotenoid-producing microorganisms from the aforementioned microbial culture, more suitable examples include methods in which, after culturing, a culture or a concentrated microbial cell solution, wet microbial cells, or dried microbial cells obtained from the culture is subjected to the following extraction treatment. The concentrate of microbial cells can be obtained, for example, by concentrating the culture by membrane filtration, and the wet microbial cells can be obtained by subjecting the culture to generally-known filtration methods such as separation by centrifugation, pressure filtration, or vacuum filtration. Furthermore, dried microbial cells can be obtained by drying the wet microbial cells by generally-known drying methods such as spray drying, fluidized drying, rotary drum-type drying, or freeze drying. In addition, at the stage of culture, microbial cell concentrate, wet microbial cells, or dried microbial cells, one, two or more treatments from among chemical treatment using an alkaline reagent, surfactant, or such, biochemical treatment using a lytic enzyme, lipolytic enzyme, protease, or such, or physical treatment such as ultrasonication or crushing may be carried out before extraction.

It is considered that, using the dried microbial cells as the standard, the microbial culture may typically contain approximately 20 mg of astaxanthin and approximately 30 mg of carotenoid in 1 g of the dried microbial cells.

(Extraction Step)

The solvent used in the extraction step of the production method of this embodiment includes a one- to three-carbon alcohol. Specifically, it is ethanol, methanol, isopropanol, or n-propanol, and among them, use of ethanol is particularly preferred. The temperature of the alcohol during extraction is preferably 80° C. or higher, more preferably 85° C. or higher, even more preferably 90° C. or higher, and particularly preferably 93° C. or higher. This temperature during extraction correlates with the increase in solubility of carotenoids including astaxanthin into the alcohol, and is an important factor for improving the extraction efficiency. The upper limit of the alcohol temperature during extraction is preferably 150° C. or lower, more preferably 130° C. or lower, even more preferably 120° C. or lower, particularly preferably 110° C. or lower, and most preferably 100° C. or lower. This upper limit temperature is important for suppressing thermal degradation of the carotenoid including astaxanthin. Here, since temperature at or above the boiling point or near the boiling point of the alcohol is required, the treatment is preferably performed in a pressure vessel. From the viewpoint of reducing the increase in cost due to the use of a pressure vessel facility, it is preferred that this pressurization is performed at a maximum gauge pressure of 0.8 MPa or lower, preferably 0.4 MPa or lower, or more preferably 0.2 MPa or lower.

The amount of alcohol used in the extraction step varies depending on the temperature during extraction, but an amount that can dissolve preferably the total amount of astaxanthin included in the microbial cells is appropriate, and is 300 g to 3,000 g, preferably 500 g to 2,000 g, and more preferably 800 g to 1,600 g per 1 g of astaxanthin included in the microbial cells.

For example, when extracting from 1 g of the dried microbial cells containing approximately 20 mg of astaxanthin using ethanol at 95° C., the amount of ethanol used may be 5 g to 100 g or so, preferably 8 g to 60 g, and more preferably 10 g to 35 g or so.

When one wants to prevent oxidation of carotenoids as much as possible in the extraction step, treatment can be performed under an atmosphere of inert gas such as nitrogen gas, or an antioxidant used for pharmaceuticals or foods may be selected and added to the extraction solvent. Alternatively, these methods may be combined.

Desirably, the antioxidant is ultimately removed from the carotenoid-containing composition; however, depending on the type of the antioxidant used (for example, when vitamin C is used), removal is unnecessary.

To minimize degradation of carotenoids due to light, the extraction may be performed under conditions where light is shielded.

While there is no need to particularly limit the extraction time, to suppress the reduction in yield of the carotenoid-containing composition due to thermal degradation, it is preferable to perform the treatment within a short period of time. The extraction time is preferably 120 minutes or less, more preferably 60 minutes or less, and most preferably 30 minutes or less.

(Extract Separation Step)

A method used for the extract separation step of the production method of this embodiment, that is, the step of separating the extract obtained by extraction treatment from microbial cells, is not limited; however, membrane filtration, filtration, decantation, and such are used, and filtration is preferred. Furthermore, the temperature for extract separation is not particularly limited. A solution in which carotenoid is dissolved in a one- to three-carbon alcohol at a temperature of 80° C. or higher is in a supersaturated state, even after cooled to −20° C. to 70° C. or so; and since the carotenoid does not precipitate within a short period of time, separation of the extract from microbial cells can be carried out stably even at such temperatures.

(Concentration Step)

In the production method of this embodiment, the extract obtained in the extract separation step is preferably concentrated at a low concentration ratio before subjecting the extract to the crystallization step detailed below. In the present invention, crystallization by concentration at a high concentration ratio is not carried out, and therefore, needle crystals or needle-like crystals with maximum length of 5 µm or longer can be obtained.

(Crystallization Step)

A method for obtaining a crystal of carotenoid-containing composition from the extract obtained by the extract separation step generally include a crystallization where the crystal solubility is decreased by heat and/or reduced-pressure concentration or addition of a poor solvent. In addition, carotenoid pigments can be separated without concentration by performing carotenoid deposition at a low temperature, or deposition using acidic/alkaline agents and various types of salts. This operation's supersaturated state is released, for example, upon leaving the solution at normal temperature for one hour or more, thus allowing crystals of carotenoid-containing composition to deposit. Stirring and agitation, addition of seed crystals, or such in this instance may accelerate the release of the supersaturated state. However, since the supersaturated state changes depending on the extraction temperature, conditions for releasing supersaturation are preferably selected depending on the extraction temperature.

When the supersaturated state is released by the above-mentioned operation, free trans-astaxanthin becomes poorly soluble in ethanol at normal temperature, and will not dissolve even upon further addition of ethanol, and becomes a suspended state. Free trans-carotenoid can be obtained as crystals by performing these operations.

In the production method of this embodiment, the extract obtained in the extract separation step is preferably concentrated at a low concentration ratio, and subsequently, crystallization of the carotenoid-containing composition is carried out by a method other than concentration.

Herein, the term "low concentration ratio" refers to a concentration ratio of less than 30-times based on the weight of the extract, and is preferably 1- to 20-times (for example, concentration ratio of 20-times or less, 15-times or less, 13-times or less, 11-times or less, or such), more preferably a concentration ratio of ten-times or less, and particularly preferably a concentration ratio of less than ten-times (for example, a concentration ratio of 8-times or less, 7-times or less, 6-times or less, 5.5-times or less, 5-times or less, or such), and the term "high concentration ratio" refers to concentration ratio of 30-times or more based on the weight of the extract, and is preferably a concentration ratio of 100-times or more, and more preferably a concentration ratio of 200-times or more.

Alternatively, "low concentration ratio" refers to concentrating up to 2.1% in terms of astaxanthin weight concentration (wt/wt) in the obtained concentrate, preferably concentrating in the range of 1.4% or less (for example, 1.1% or less, 0.91% or less, 0.77% or less, or such), more preferably concentrating in the range of 0.70% or less, particularly preferably concentrating in the range of up to 0.70% (for example, 0.56% or less, 0.49% or less, 0.42% or less, 0.39% or less, 0.35% or less, or such), and "high concentration ratio" refers to 2.1% or more, preferably 7.0% or more, and more preferably 14% or more in terms of astaxanthin weight concentration (wt/wt).

Alternatively, "low concentration ratio" refers to concentrating up to 3.0% in terms of carotenoid weight concentration (wt/wt) in the obtained concentrate, preferably concentrating in the range of 2.0% or less (for example, 1.5% or less, 1.3% or less, 1.1% or less, or such), more preferably concentrating in the range of 1.0% or less, or particularly preferably concentrating in the range of up to 1.0% (for example, 0.80% or less, 0.70% or less, 0.60% or less, 0.55% or less, 0.50% or less, or such), and "high concentration ratio" refers to 3.0% or more, preferably 10% or more, and more preferably 20% or more in terms of carotenoid weight concentration (wt/wt).

More specifically, examples of the concentration ratio may include 1.25-times to 20-times, more specifically 1.25-times to 10-times, and even more specifically twice to 10-times.

Alternatively, examples of the astaxanthin weight concentration (wt/wt) may include 0.088% to 1.4%, more specifically 0.088% to 0.70%, and even more specifically 0.14% to 0.70%.

Alternatively, examples of the carotenoid weight concentration (wt/wt) may include 0.13% to 2.0%, more specifically 0.13% to 1.0%, and even more specifically 0.20% to 1.0%.

The concentration step is preferably carried out by heat concentration where an extraction solvent is distilled off by heating, or by reduced-pressure concentration where an extraction solvent is distilled off under reduced pressure. From the viewpoint of suppressing carotenoid degradation, concentration by reduced-pressure concentration which allows the vessel temperature to be kept low is more preferred. The preferred vessel temperature for reduced-pressure concentration is 50° C. or lower, more preferably 40° C. or lower; and from the viewpoint of efficiency of distilling off the solvent, the vessel temperature is preferably 0° C. or higher, and more preferably 10° C. or higher.

The distillate obtained by concentrating the extract can be reused as it is for extraction from microbial cultures.

(Aging Step)

Methods used in the crystallization step of the production method of this embodiment, that is, the step of generating crystals of carotenoid-containing compositions in the aforementioned concentrate, are not limited, but for example, an aging step where crystals are obtained by incubating the aforementioned concentrate at 10° C. to 60° C. is used. The temperature during aging is preferably 10° C. to 60° C., more preferably 20° C. to 40° C., and particularly preferably 30° C. The duration suitable for aging is preferably 1 hour to 48 hours, more preferably 2 hours to 24 hours, and particularly preferably overnight.

(Heating Step)

Prior to the aging step, one can further add a heating step where the concentrate is incubated at a temperature higher than the temperature for the aging step in order to deposit a portion of trans-carotenoid isomers in the concentrate as crystals, as well as to isomerize at least a portion of cis-carotenoid isomers to the trans-isomers.

The temperature of this heating step is higher than the temperature for the aging step, and is preferably the boiling point under normal pressure of the one- to three-carbon alcohol which is the solvent of the concentrate or below. Specifically, the temperature is preferably 30° C. to 80° C., more preferably 40° C. to 70° C., and particularly preferably 50° C. to 60° C. The duration of treatment in this heating step is preferably 1 hour to 48 hours, more preferably 2 hours to 26 hours, and particularly preferably 2 hours to 8 hours.

This heating step may also be carried out concurrently with the concentration step. That is, performing this isomerization by maintaining a high temperature during reduced-pressure concentration will be effective for shortening the time taken for the steps.

Adding a heating step prior to the aging step increases the amount of crystals of carotenoid-containing composition obtained through the aging step. More specifically, it increases the yield of carotenoid-containing composition obtained by the production method of this embodiment.

The present inventors think that the following takes place in the heating step.

The extraction step of the production method of this embodiment is performed at 80° C. or higher which is a relatively a high temperature; therefore, a portion of the trans isomers of the carotenoid is isomerized to the cis isomers. Such carotenoid-containing extracts become supersaturated concentrates through the concentration step. This supersaturated state of the concentrate is released in the heating step, and leads to crystallization of a portion of the trans-carotenoid isomers which have relatively low solubility to a one- to three-carbon alcohol, whereas the cis-carotenoid isomers which have relatively high solubility to the aforementioned alcohol remain dissolved in the alcohol. Then, the cis/trans ratio for the carotenoid isomers dissolved in the solvent increases, and the ratio deviates from the equilibrium composition at that temperature. This deviation from the equilibrium composition and increase in the reaction speed of isomerization reaction as a result of heating the concentrate together lead to isomerization of a portion of the cis isomers to trans isomers. A portion of the trans isomers generated by the isomerization is crystallized.

Along with crystallization of the trans isomers, isomerization from the cis isomers to the trans isomers is thought to be advanced in the aging step as well; however, since the temperature is higher in the heating step than in the aging step, the isomerization reaction rate is higher and the isomerization is further advanced.

After the heating step, by subjecting the concentrate containing the crystals obtained from this step to an aging step at a temperature lower than that in the heating step, carotenoids, mainly the trans isomers dissolved in the solvent, further crystallize.

In this manner, by increasing the ratio of the trans isomers through adding a heating step, the yield of the crystal of carotenoid-containing composition, which is the target substance of the production method of this embodiment, can be improved.

(Water Addition Step)

Prior to the heating step, a water addition step where water is added to the concentrate obtained by the concentration step may further be included. The amount of water added in this water addition step is an amount where the concentration of water in the solution after the addition becomes preferably 0.1 to 40 mass %, more preferably 0.5 to 30 mass %, and particularly preferably 1 to 20 mass %.

Furthermore, this water addition step can be carried out along with the concentration step. That is, water may be added to the carotenoid-containing extract prior to concentrating or during concentrating the solution.

Adding a water addition step prior to the heating step reduces the solubility of the carotenoid in the carotenoid-containing solution, and the crystal amount of carotenoid-containing composition obtained through the heating step and the aging step increases. More specifically, this increases the yield of the carotenoid-containing composition obtained by the production method of this embodiment.
(Crystal Separation Step)

A method used in the crystal separation step of the production method of this embodiment, that is, the step of separating and obtaining the crystals produced in the aging step from the mother liquor is not limited; however, filtration, centrifugation, or such may be used, and filtration is preferred. The temperature at which the crystals are separated is not particularly limited.

The separated crystals of the carotenoid-containing composition are preferably washed. The washing methods are not particularly limited, but washing using a solvent such as a one- to three-carbon alcohol at normal temperature, a mixture of the aforementioned alcohol and water, or a hydrocarbon such as hexane is preferably used. Washing can be carried out, for example, by pouring the aforementioned solvent onto a cake of crystals separated by filtration.

The crystals of the carotenoid-containing composition that have undergone the crystal separation step or the following washing step are preferably dried. The drying methods are not particularly limited, and drying by heating at a normal pressure under inert atmosphere or drying under reduced pressure may be used; drying under reduced pressure is preferred.

A specific example of a method of producing a carotenoid-containing composition of the present invention includes the following method; however, obviously the present invention is not limited thereto:
1) extraction from astaxanthin-containing microbial cells using ethanol at 90° C. to 100° C. for 15 minutes or longer;
2) removal of microbial cells by thermal filtration (60° C. to 70° C.);
3) cooling the filtrate (extract) to 30° C., adjusting the pressure reduction degree so that the vessel temperature becomes 30° C., and concentrating so that the amount of liquid becomes ⅕ (astaxanthin weight concentration of 0.35% (wt/wt) or carotenoid weight concentration of 0.50% (wt/wt) or so);
4) after concentration, aging at 30° C.;
5) after aging, recovery of crystals by filtration; and
6) drying the crystals by heating at 100° C. under vacuum.

After the concentration step of 3), the cis isomers of astaxanthin can be re-isomerized to the trans isomers by heating at 60° C. for two to four hours, and then the method can proceed to step 4). This re-isomerization can also be carried out at 50° C., and the duration may be lengthened to increase efficiency. When re-isomerization is carried out at 40° C., the duration may be lengthened further.

Furthermore, after the concentration step of 3), the method can proceed to step 4) after adding water to the concentrate at a final concentration of 1 to 20 mass %. This water addition can be carried out by addition of water in an amount that yields a final water concentration of 0.1 to 40 mass %, more preferably addition of water in an amount that yields 0.5 to 30 mass %, and particularly preferably addition of water in an amount that yields 1 to 20 mass %.

The carotenoid content and the content of the main component such as astaxanthin included in the carotenoid-containing composition obtained using the above-mentioned production method can be adjusted by appropriately changing the conditions of each step of the production method to maximize the yield. The carotenoid content in the carotenoid-containing composition of the present invention is specified by the amount of astaxanthin in the carotenoids in the microbial cells. When the E-396 strain or its mutant strain is used as the microbial cells, a carotenoid-containing composition containing 40% or more astaxanthin based on the composition can be obtained.

As described above, the method of producing a carotenoid-containing composition of this embodiment is characterized in that after the culture of a carotenoid-producing microorganism is extracted using a one- to three-carbon alcohol, the extract is concentrated to an appropriate concentration ratio under reduced pressure, and then crystals of the carotenoid-containing composition are generated in the concentrate. A highly pure carotenoid can be obtained by using only these very simple operations, and a subsequent complicated repulping step can be avoided.

Compared to conventional technology, the method of producing the carotenoid-containing composition of this embodiment is remarkably advantageous from an industrial viewpoint in that it: 1) does not require complicated operations; 2) does not require a complicated and inefficient washing operation such as washing by suspension or repulping the concentrated dried solid material; and 3) does not require treatment of waste solution containing water, excluding the case where a water addition step is included before the heating step. Furthermore, the production method provides an excellent industrial production method in that: 4) the method can economically provide a highly pure carotenoid-containing composition which has a high astaxanthin content; and 5) powder properties, formability, and such of the obtained crystals are satisfactory.

The present invention also provides a carotenoid-containing composition derived from a microorganism which produces carotenoid including astaxanthin, wherein the astaxanthin content is 40 mass % or more (or 40 to 90 mass %) and the carotenoid content is 70 mass % or more (or 70 to 100 mass %) based on the mass of the total composition, and wherein the carotenoid-containing composition is a needle crystal or a needle-like crystal having a maximum length of 5 μm or longer.

The maximum crystal length is preferably 7 μm or longer, and more preferably 10 μm or longer.

The carotenoid-containing composition of the present invention is preferably produced by the above-described method of producing a carotenoid-containing composition of the present invention.

Pharmaceuticals, foods, or cosmetics comprising a carotenoid-containing composition of the present invention are also within the scope of the present invention.

Pharmaceuticals comprising a carotenoid-containing composition of the present invention are available in formulations including powders, granules, pills, soft capsules, hard capsules, tablets, chewable tablets, disintegrating tablets, syrups, solutions, suspensions, suppositories, ointments, creams, gels, patches, inhalants, and injections. These formulations are prepared in accordance with an established method. Carotenoids are hardly soluble in water, and so are used dissolved in a non-hydrophilic organic solvent such as a vegetable or animal oil, dispersed or emulsified in an aqueous solution together with an emulsifier, a dispersant, a surfactant or the like using a homogenizer (high pressure homogenizer), or heat dissolved. In order to improve the absorbability of carotenoids, they may be used after being pulverized to an average particle diameter as small as about 1 micrometer.

Additives usable for producing the formulations include, for example, animal and vegetable oils such as soybean oil, safflower oil, olive oil, germ oil, sunflower oil, grape seed oil, beef tallow, and sardine oil; polyhydric alcohols such as polyethylene glycol, propylene glycol, glycerin, and sorbitol; surfactants such as sorbitan fatty acid ester, sucrose fatty acid ester, glycerin fatty acid ester, and polyglycerin fatty acid ester; excipients such as purified water, lactose, starch, crystalline cellulose, D-mannitol, lecithin, gum arabic, sorbitol solution, and sugar solution; sweeteners, coloring agents, pH adjusters, flavor substances. A liquid formulation may be dissolved or suspended in water or any other appropriate medium when being administered. A tablet or a granule may be coated by a well-known method, or wrapped in a sol- or gel-like substance or the like.

Administration by injection is preferably performed intravenously, intraperitoneally, intramuscularly, subcutaneously, percutaneously, intra-articularly, in synovial bursa, in bulla, in periosteum, sublingually, orally or the like, and is particularly preferably performed intravenously or intraperitoneally. The intravenous administration may be drip administration or bolus administration.

When carotenoids are used as pharmaceuticals, the daily dose for an adult is 1 mg to 3 g, preferably 3 mg to 1 g, and more preferably 10 mg to 670 mg. When converted to an amount per 1 kg of the body weight, such doses are, respectively, 17 µg to 50 mg, 54 µg to 17 mg, and 160 µg to 12 mg. Such a dose is administered once a day or divided into several times a day. The pharmaceutically effective amount, administration method, administration means and administration period can be appropriately set by a person of ordinary skill in the art in accordance with the clinical state, gender, age, body weight or the like of each administered subject.

Foods comprising a carotenoid-containing composition of the present invention are available as, for example, supplements (powders, granules, soft capsules, hard capsules, tablets, chewable tablets, disintegrating tablets, syrups, solutions, etc.), drinks (tea, carbonated drinks, lactic drinks, sports drinks, etc.), confectionaries (gummi, jelly, chewing gum, chocolate, cookie, candy, etc.), oils, fats and oils foods (mayonnaise, dressing, butter, cream, margarine, etc.), seasonings (ketchup, sauce, etc.), liquid foods, dairy products (milk, yogurt, cheese, etc.), breads, and noodles (udon, soba, ramen, pasta, fried noodle, kishimen, somen, hiyamugi, bihon, etc.). The foods are not limited to the above.

Functional foods comprising a carotenoid-containing composition of the present invention may contain, as necessary, any of various nutrients, various vitamins (vitamin A, vitamin B1, vitamin B2, vitamin B6, vitamin B12, vitamin C, vitamin E, etc.), various minerals, dietary fiber, polyunsaturated fatty acid, other nutrients (coenzyme Q10, carnitine, sesamine, α-lipoic acid, inositol, D-chiroinositol, pinitol, phosphatidylserine, phosphatidyl DHA, phosphatidyl inositol, taurine, glucosamine, chondroitin sulfate, S-adenosylmethionine, etc.), stabilizers such as dispersants and emulsifiers, sweeteners, taste enriching components (citric acid, malic acid, etc.), flavor substances, royal jelly, propolis, agaricus, and the like. Herbs such as peppermint, bergamot, chamomile, lavender, and thyme can be also contained. Elements such as theanine, dehydroepiandrosterone, and melatonin can also be blended.

When carotenoids are used as a food or as a supplement, there is no specific limitation on the dose or manner of administration. The dose may be 17 µg to 50 mg, preferably 54 µg to 17 mg, and more preferably 160 µg to 12 mg, when converted to dose per 1 kg of body weight.

Cosmetic products comprising a carotenoid-containing composition of the present invention include creams, milky lotions, lotions, micro-emulsion essence, and bathwater additives, and may contain a fragrance or the like.

When carotenoids are used as a cosmetic product, the dose is 10 µg to 5 g, preferably 10 µg to 2 g, and more preferably 10 µg to 1 g, per 100 g of the cosmetic product.

All prior art documents cited herein are incorporated herein as references.

EXAMPLES

The present invention will be described based on examples. However, the scope of the present invention is not limited to the following examples.

In the examples and comparative examples, astaxanthin and carotenoids were quantified by high performance liquid chromatography (HPLC). Two columns of Wakosil-II SIL-100 (Ø4.6×250 mm) (produced by Wako Pure Chemical Industries, Ltd.) were connected to each other to be used as a column. Elution was performed by flowing an n-hexane/tetrahydrofuran/methanol mixed solution (capacity ratio 40:20:1), which was the mobile phase, at a flow rate of 1.0 ml/min. at a constant temperature around room temperature. The measurement was performed as follows. The sample was dissolved in tetrahydrofuran, and the resultant substance was diluted 100-fold with the mobile phase. 20 µL of the resultant solution was injected. Carotenoid in the column elution solution was detected at a wavelength of 470 nm. As the standard solution for quantification, astaxanthin produced by Sigma (Cat. No. A9335) was used. The astaxanthin concentration of the standard solution was set using the following equation after measuring the absorbance of the standard solution of 477 nm (A) and the area percentage % (B) of the astaxanthin peak at the time of HPLC analysis under the above-described conditions.

$$\text{Astaxanthin concentration (mg/L)} = A/2150 \times B \times 100 \quad (1)$$

Sample Preparation Method

Hereinafter, tetrahydrofuran containing 250 ppm butylhydroxytoluene, which is an antioxidant, is used. In a 50-mL glass centrifugation tube, 50 mg to 80 mg of dried microbial cells were precisely weighed, and then 150 µL of distilled water was added to wet the microbial cells. Then, 15 mL of tetrahydrofuran-methanol solution (20:1) was added to this, and after mixing thoroughly for five minutes, 30 mL of hexane was added. Microbial cells were precipitated from this solution by centrifugation, the supernatant was diluted ten times using the mobile phase for HPLC, and then HPLC analysis was performed.

Calculation Method

Astaxanthin concentration was calculated according to equation (2), canthaxanthin concentration was calculated according to equation (3), and the concentration of other carotenoids was calculated according to equation (4).

$$\text{Astaxanthin (mg/g)} = (\text{astaxanthin concentration in the standard solution (mg/L)})/(\text{peak area for the astaxanthin standard solution}) \times (\text{peak area for astaxanthin in the sample})/(\text{sample mass (mg)}) \times 450 \quad (2)$$

The canthaxanthin concentration was calculated according to equation (3).

$$\text{Canthaxanthin (mg/g)} = (\text{astaxanthin concentration in the standard solution (mg/L)})/(\text{peak area for the astaxanthin standard solution}) \times (\text{peak area for canthaxanthin in the sample})/(\text{sample mass (mg)}) \times 450 \times 0.92 \quad (3)$$

The carotenoid concentration was calculated according to equation (4).

$$\text{Carotenoid (mg/g)} = (\text{astaxanthin concentration in the standard solution (mg/L)})/(\text{peak area for the astaxanthin standard solution}) \times (\text{peak area for carotenoid in the sample})/(\text{sample mass (mg)}) \times 450 \quad (4)$$

Example 1

Production of a Highly Pure Carotenoid with a High Astaxanthin Content: 1 (FIG. 1)

Step 1: E-396 Strain Culturing Step

E-396 strain was cultured according to the method described in Example 1 of Patent Document 5, and dried bacterial cells containing carotenoids including approximately 17 mg of astaxanthin in 1 g of the cells as a culture were obtained.

Step 2: Ethanol Extraction Step

To 25 g of dried bacterial cells obtained in Step 1 of this Example, 550 g of ethanol was added and carotenoids including astaxanthin were extracted by stirring for 15 minutes at 90° C. under nitrogen atmosphere in a high-pressure vessel. After cooling the liquid temperature to 65° C., the pressure vessel was opened, bacterial cells were removed from the extract by filtration, and then the bacterial cell cake was washed with ethanol to obtain 550 g of extract with 0.07% (wt/wt) astaxanthin and 0.1% (wt/wt) carotenoids in terms of weight concentration.

Subsequently, a similar operation was repeated six more times, and a total of seven batches of extract were obtained.

Step 3: Step of Concentrating the Extract and Performing Crystallization

One batch of the extract obtained in Step 2 of this Example was subjected to reduced pressure adjustment to make the vessel temperature 30° C., and a portion of the ethanol was distilled off using a rotary evaporator so that the solid concentration was 1.25-times concentrated than the extract. Then, this concentrate was aged overnight at a vessel temperature of 30° C. to deposit the crystals.

Furthermore, the extracts of the other six batches obtained in Step 2 of this Example were subjected to the same operations as described above, except that the concentration rate was 1.5-times, 2-times, 3.3-times, 5-times, 10-times, 20-times, respectively, to perform concentration and crystallization.

Step 4: Steps of Filtering out the Crystals and Drying Them

Crystals were recovered by filtration from each of the crystal-containing solutions obtained in Step 3 of this Example. The respective crystals were dried under reduced pressure at 100° C. for two hours to obtain dried crystals. The astaxanthin and carotenoid contents of these dried crystals were determined by the aforementioned method, and the amount of the recovered crystals and the recovery efficiency of astaxanthin are both shown in Table 1.

The crystals obtained at a five-time concentration ratio, indicated in Table 1, were photographed at a 200 magnification using a digital microscope (KEYENCE, VHX-90), and the size of the crystals were determined. The crystals included portions that were 10 μm or longer.

As shown in Table 1, high-carotenoid-content compositions could be recovered by the method of this Example, which is a very simple method, from a culture of a carotenoid-producing microorganism. In conventional methods, as extracts obtained in a manner similar to Step 1 of this Example were concentrated under reduced pressure at a high concentration ratio, the obtained concentrates were viscous liquids or concentrated dry solids and recovery was difficult. In this case, a step such as suspending and washing step performed by solvent addition was necessary. However, addition of a poor solvent such as water brings impurities, which results in poor filtration properties; therefore, a further washing step (repulping step) was required to increase the content, and the operation was complicated (for example, after concentration at a temperature of 60° C. with a high concentration ratio, first, water is added to lower the solubility, and then ethanol is added for suspension and washing, then this is filtered, and after further washing of the filtrate using ethanol, a drying step is performed). In addition, since a lower alcohol solution containing water becomes the filtrate (waste solution), treatment of this waste solution was difficult due to the high BOD load. When performing a combustion treatment, the caloric value is low as the waste solution contains water, and a large amount of a combustion improver was necessary. On the other hand, the method of this Example achieved improvements such as (1) simple handling of the concentrate as the concentration rate is suppressed to an appropriate degree, (2) satisfactory filtration properties since by carrying out the crystallization from the concentrate, crystals with good crystal form (needle or needle-like form) which includes portions that are 5 μm or longer can be obtained, (3) easy recovery of the obtained crystalline powder since it hardly adheres to the container and such, and has satisfactory properties such as being granular, which hardly flutters and is satisfactorily moldable, and (4) easy combustion treatment since water is not contained in the waste solution.

Comparative Example 1

The E-396 strain was cultured according to the method of Example 1 in Patent Document 5 and dried bacterial cells containing carotenoids including approximately 17 mg of astaxanthin in 1 g of cells as a culture were obtained. Furthermore, crystals of a carotenoid-containing composition including astaxanthin were obtained according to Example 1 of Patent Document 6. These crystals were photographed using a digital microscope by a method similar to that of Example 1, and the size of the crystals was determined. The crystal size was 1 μm to 2 μm.

TABLE 1

|  | CONCENTRATION RATE | | | | | | |
| --- | --- | --- | --- | --- | --- | --- | --- |
|  | 1.25 TIMES | 1.5 TIMES | 2 TIMES | 3.3 TIMES | 5 TIMES | 10 TIMES | 20 TIMES |
| ASTAXANTHIN CONCENTRATION IN CONCENTRATE (wt/wt) | 0.088% | 0.11% | 0.14% | 0.23% | 0.35% | 0.70% | 1.4% |
| CAROTENOID CONCENTRATION IN CONCENTRATE (wt/wt) | 0.13% | 0.15% | 0.20% | 0.33% | 0.50% | 1.0% | 2.0% |
| CRYSTAL AMOUNT | 185 mg | 257 mg | 285 mg | 324 mg | 366 mg | 388 mg | 410 mg |
| ASTAXANTHIN RECOVERY EFFICIENCY | 27% | 37% | 41% | 45% | 50% | 53% | 56% |
| ASTAXANTHIN CONTENT | 62% | 61% | 61% | 59% | 58% | 58% | 54% |
| CAROTENOID CONTENT | 98% | 97% | 98% | 93% | 94% | 94% | 78% |

Example 2

Production of a Highly Pure Carotenoid with a High Astaxanthin Content: 2

Figure 2:
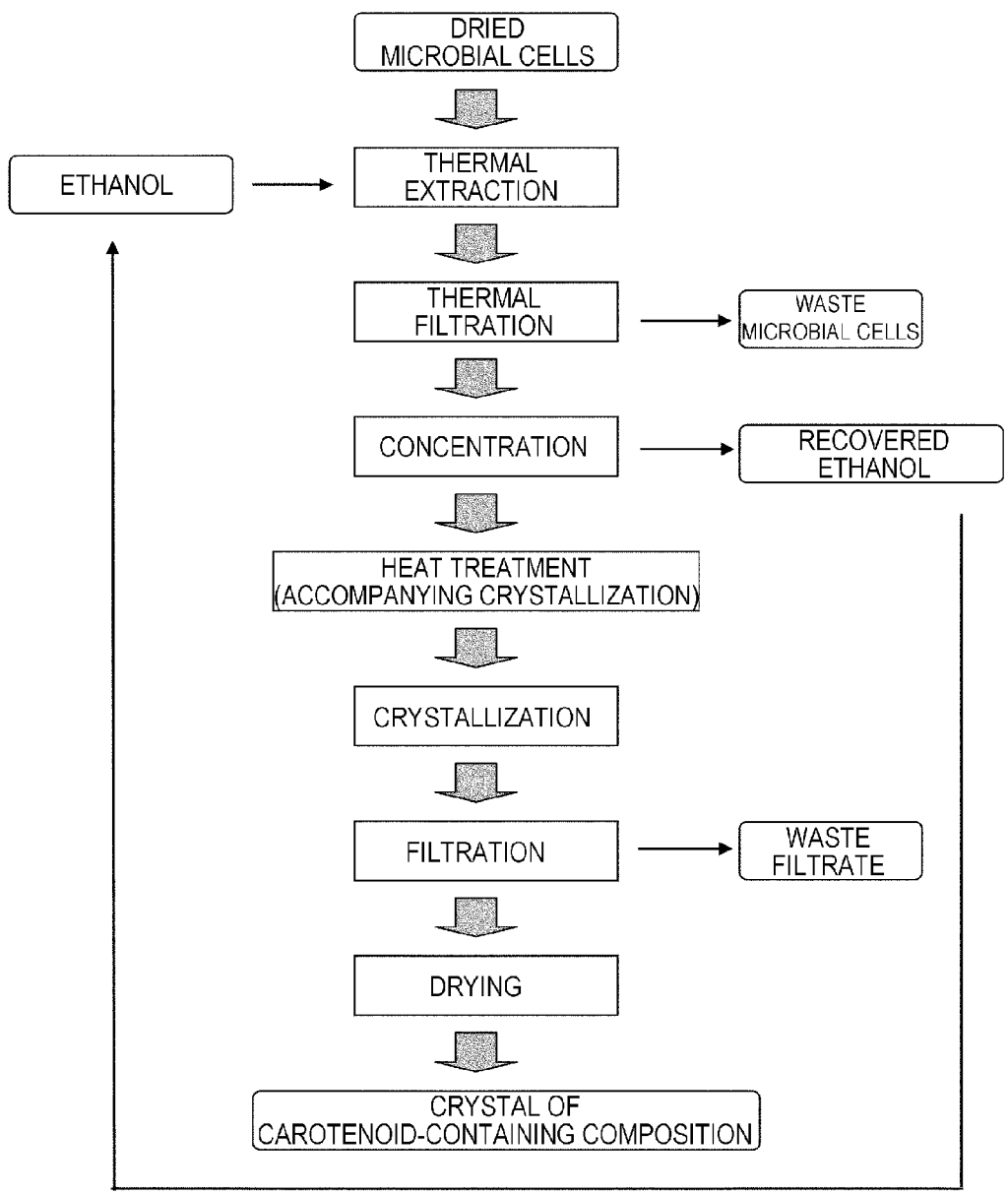
FIG. 2 shows an embodiment of the present invention for producing a composition which contains carotenoids including astaxanthin from dried microbial cells which contain carotenoids including astaxanthin. This embodiment is characterized in that it includes a step of re-isomerization by heat treatment after concentrating the extract.

(A Production Method that Comprises an Isomerization Step after the Concentration Step: FIG. 2)

Step 1: E-396 Strain Culturing Step

Dried bacterial cells containing carotenoids including approximately 17 mg of astaxanthin in 1 g of the cells were obtained in a manner similar to the above-mentioned Step 1 of Example 1.

Step 2: Ethanol Extraction Step 550 g of a similar extract was obtained by an operation similar to the above-mentioned Step 2 of Example 1. Subsequently, a similar operation was repeated four more times to obtain a total of five batches of extract.

Step 3: Step of Concentrating the Extract, and Performing Heat Treatment (Incubation) and Crystallization The extract obtained in Step 2 of this Example was subjected to reduced pressure adjustments to make the vessel temperature 30° C., and a portion of the ethanol was distilled off using a rotary evaporator so that the solid concentration became five times concentrated than the extract (astaxanthin weight concentration of 0.35% (wt/wt) and carotenoid weight concentration of 0.50% (wt/wt)). Subsequently, this concentrate was subjected to heat (incubation) treatment under nitrogen atmosphere at 40° C. for 25.5 hours, and then aged overnight at a vessel temperature of 30° C. to deposit the crystals.

Furthermore, concentration, heat treatment, and crystallization were performed on each of the other four batches of extracts obtained in step 2 of this Example by the same operations as described above, except that the duration and temperature of the heat treatment were set to conditions shown in Table 2, respectively.

Step 4: Steps of Filtering out the Crystals, and Washing and Drying Them

Crystals were recovered by filtration from the crystal-containing solution obtained in Step 3 of this Example. These crystals were dried under reduced pressure at 100° C. for two hours to obtain dried crystals. The astaxanthin and carotenoid contents of these dried crystals were determined by the aforementioned method, and the amount of the recovered crystals and the recovery efficiency of astaxanthin are shown in Table 2.

TABLE 2

|  | HEAT TREATMENT TEMPERATURE | | | | |
| --- | --- | --- | --- | --- | --- |
|  | 40° C. | 50° C. | 60° C. | 60° C. | 60° C. |
| HEAT TREATMENT TIME | 25.5 HOURS | 7.5 HOURS | 2 HOURS | 4 HOURS | 7.5 HOURS |
| CRYSTAL AMOUNT | 413 mg | 440 mg | 396 mg | 425 mg | 432 mg |
| ASTAXANTHIN RECOVERY EFFICIENCY | 58% | 58% | 55% | 59% | 59% |
| ASTAXANTHIN CONTENT | 58% | 56% | 59% | 59% | 58% |
| CAROTENOID CONTENT | 93% | 89% | 94% | 94% | 92% |

As shown in Table 2, by performing heat treatment after the concentration, the amount of crystals recovered and the recovery efficiency of astaxanthin were confirmed to be improved compared to the case when the conditions for the concentration ratio in Table 1 are the same (five-time concentration ratio), but without performing heat treatment. The reason for this may be as follows: a portion of trans astaxanthin which was isomerized to cis astaxanthin (which readily dissolves in ethanol at normal temperature) by an equilibration reaction under high temperature conditions during extraction was dissolved in ethanol during aging (crystallization), but as trans astaxanthin left the system by crystallization, equilibrium deviated and the reaction speed increased due to heat treatment, and then the amount dissolved in the filtrate decreased due to re-isomerization of a portion of cis astaxanthin by an equilibration reaction to trans astaxanthin which is poorly soluble in ethanol.

Thus, it was shown that by merely including a simple heat treatment step after the concentration step, the yield of a carotenoid-containing composition can be improved without lowering the astaxanthin content and carotenoid content in the carotenoid-containing composition.

Example 3

Production of a Highly Pure carotenoid with a High Astaxanthin Content: 3

Figure 3:
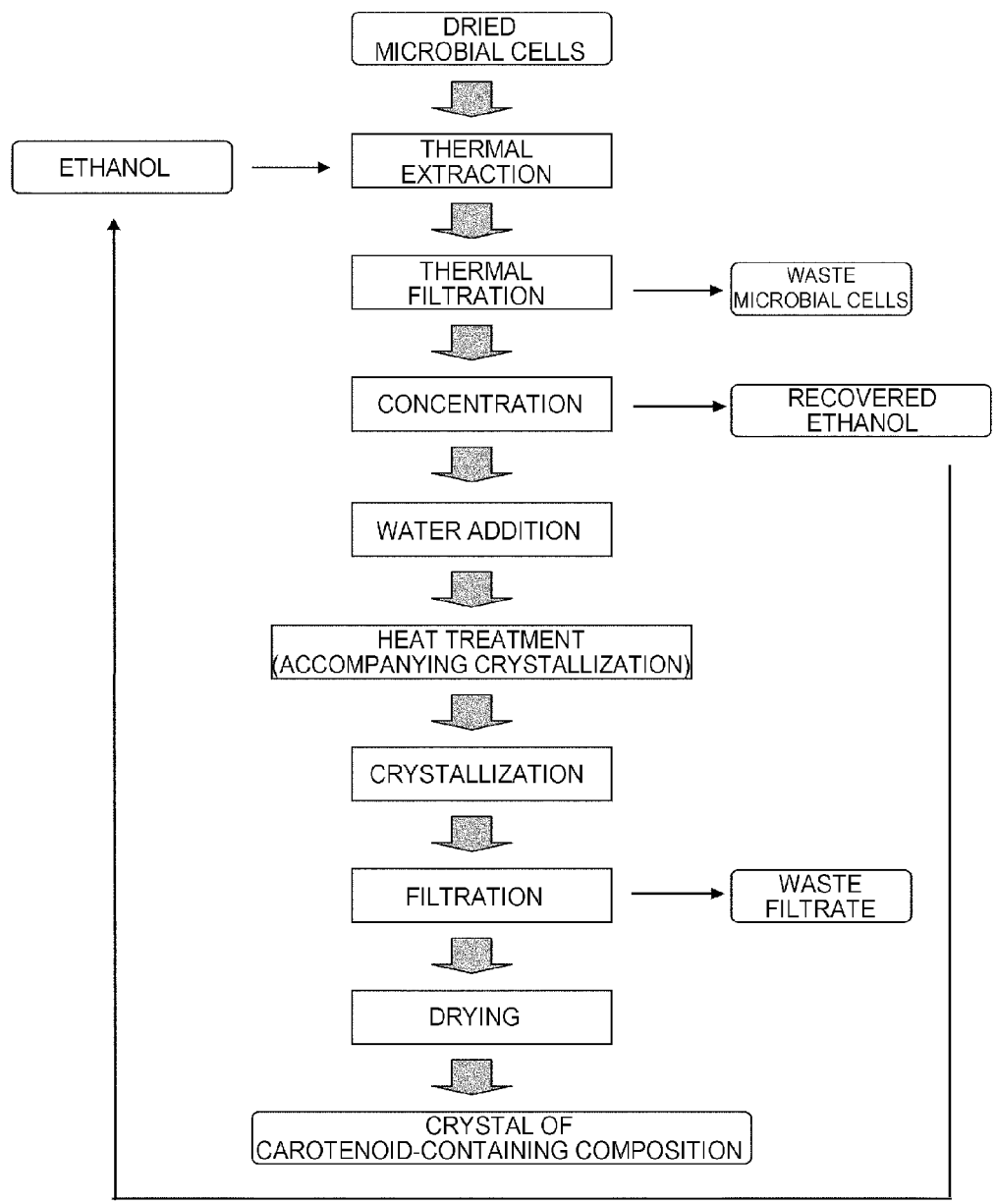
FIG. 3 shows an embodiment of the present invention for producing a composition which contains carotenoids including astaxanthin from dried microbial cells which contain carotenoids including astaxanthin. This embodiment is characterized in that it includes a step of adding water after concentrating the extract and before heat treatment.

(A Production Method Comprising a Water Addition Step and an Isomerization Step Following Concentration: FIG. 3)

Step 1: E-396 Strain Culturing Step

Dried bacterial cells containing carotenoids including approximately 17 mg of astaxanthin in 1 g of the cells were obtained in a manner similar to the above-mentioned Step 1 of Example 1.

Step 2: Ethanol Extraction Step 550 g of a similar extract was obtained by an operation similar to the above-mentioned Step 2 of Example 1. Subsequently, a similar operation was repeated five more times to obtain a total of six batches of extract.

Step 3: Steps of Concentrating the Extract, Adding Water, and Performing Heat Treatment (Incubation) and Crystallization The extract obtained in Step 2 of this Example was subjected to reduced pressure adjustments to make the vessel temperature 30° C., and a portion of the ethanol was distilled off using a rotary evaporator so that the solid concentration became five times concentrated than the extract (astaxanthin weight concentration of 0.35% (wt/wt) and carotenoid weight concentration of 0.50% (wt/wt)). Ion exchange water was added to five of the six batches of concentrate at 1, 3, 5, 10, and 20 weight %, respectively. These solutions with or without ion exchange water addition were subjected to heat (incubation) treatment under nitrogen atmosphere at 60° C. for two hours, and then aged overnight at a vessel temperature of 30° C. to deposit the crystals.

Step 4: Steps of Filtering Out the Crystals, and Washing and Drying Them

Crystals were recovered by filtration from the crystal-containing solution obtained in Step 3 of this Example. These crystals were dried under reduced pressure at 100° C. for two hours to obtain dried crystals. The astaxanthin and carotenoid contents of these dried crystals were determined by the aforementioned method and the amount of the recovered crystals and the recovery efficiency of astaxanthin are both shown in Table 3.

TABLE 3

| | ADDITIVE WATER AMOUNT (wt/wt) | | | | | |
|---|---|---|---|---|---|---|
| | 0% | 1% | 3% | 5% | 10% | 20% |
| CRYSTAL AMOUNT (mg) | 364 | 404 | 430 | 428 | 445 | 536 |
| ASTAXANTHIN RECOVERY EFFICIENCY | 55% | 61% | 63% | 64% | 64% | 71% |
| ASTAXANTHIN CONTENT | 64% | 64% | 62% | 63% | 61% | 57% |
| CAROTENOID CONTENT | 94% | 93% | 92% | 95% | 92% | 87% |

As shown in Table 3, by adding water after the concentration and before the heat treatment, the amount of crystals recovered and the recovery efficiency of astaxanthin were confirmed to be improved compared to when water was not added before heat treatment. The reason for this may be that the solubility of carotenoids in the carotenoid-containing solution decreased due to water addition.

Thus, it was shown that by merely including the simple step of adding water after the concentration and before the heat treatment, the yield of a carotenoid-containing composition can be improved without greatly lowering the astaxanthin content and carotenoid content in the carotenoid-containing composition.

INDUSTRIAL APPLICABILITY

The present invention enables methods of producing carotenoid-containing compositions in which the compositions can be obtained at a high yield through simple steps using economical and safe solvents; the carotenoid-containing compositions are derived from a microorganism, have a high astaxanthin content and contain highly pure carotenoids, and also have satisfactory crystal properties. The present invention also provides the aforementioned carotenoid-containing compositions.

The invention claimed is:

1. A method of producing a crystallized carotenoid-containing composition that is a needle crystal wherein the maximum length of crystals is 5 μm or longer, and whose astaxanthin content based on the total composition is 50 mass % or more, wherein the method comprises:
   an extraction step where a culture obtained by culturing a microorganism that produces carotenoids including astaxanthin is extracted using a one- to three-carbon alcohol;
   an extract separation step where an extract is obtained by separating the microorganism and the extract;
   a concentration step where a concentrate is obtained by concentrating the extract by 1.25-times to 20-times in terms of liquid quantity;
   a heating step wherein the solution is heated to a temperature higher than the temperature for the crystallization step thereby causing isomerization of cis-carotenoid isomers to transisomers;
   a crystallization step where crystals of the carotenoid-containing composition are produced in the concentrate; and
   a crystal separation step where the crystals are separated and obtained from mother liquor; wherein the crystal is a needle crystal having an astaxanthin content, based on the mass of the total composition, of 50 mass % or more, and wherein the maximum length of crystals is 5 μm or longer.

2. The method of producing a carotenoid-containing composition of claim 1, wherein the concentration ratio is less than ten-times in the concentration step.

3. The production method of claim 1, which further comprises a step selected from the group consisting of: a water-addition step where water is added to the concentrate before the heating step; a water-addition step where water is added to the concentrate during the concentration step; and a water-addition step where water is added to the extract separated from the microorganism before the concentration step.

4. The production method of claim 1, wherein the temperature used in the heating step is 40° C. to 70° C.

5. The method, according to claim 1, wherein the temperature used in the heating step is 40° C. to 70° C.

6. A crystallized carotenoid-containing composition produced by a method comprising:
   an extraction step where a culture obtained by culturing a microorganism that produces carotenoids including astaxanthin is extracted using a one- to three-carbon alcohol;
   an extract separation step where an extract is obtained by separating the microorganism and the extract;
   a concentration step where a concentrate is obtained by concentrating the extract by 1.25-times to 20-times in terms of liquid quantity;
   a heating step wherein the solution is heated to a temperature higher than the temperature for the crystallization step thereby causing isomerization of cis-carotenoid isomers to trans-isomers,
   a crystallization step where crystals of the carotenoid-containing composition are produced in the concentrate; and
   a crystal separation step where the crystals are separated and obtained from mother liquor; wherein the crystal is a needle crystal having an astaxanthin content, based on the mass of the total composition, of 50 mass % or more, and wherein the maximum length of crystals is 5 μm or longer.

7. The crystallized carotenoid-containing composition of claim 6, wherein the concentration ratio is less than ten-times in the concentration step.

8. The crystallized carotenoid-containing composition of claim 6, wherein the method further comprises a step selected from the group consisting of: a water-addition step where water is added to the concentrate before the heating step; a water-addition step where water is added to the concentrate during the concentration step; and a water-addition step where water is added to the extract separated from the microorganism before the concentration step.

9. The crystallized carotenoid-containing composition of claim 6, wherein the temperature used in the heating step is 40° C. to 70° C.

* * * * *